United States Patent [19]

Allen

[11] Patent Number: 4,837,028

[45] Date of Patent: Jun. 6, 1989

[54] LIPOSOMES WITH ENHANCED CIRCULATION TIME

[75] Inventor: Theresa M. Allen, Edmonton, Canada

[73] Assignee: Liposome Technology, Inc.

[21] Appl. No.: 946,415

[22] Filed: Dec. 24, 1986

[51] Int. Cl.[4] .................. A61K 9/66; A61K 37/22; B01J 13/02

[52] U.S. Cl. .................. 424/450; 264/4.3; 424/1.1; 428/402.2; 435/5; 436/829

[58] Field of Search .................. 428/402.2; 424/450; 436/829

[56] References Cited

U.S. PATENT DOCUMENTS

| | | | |
|---|---|---|---|
| 4,416,872 | 11/1983 | Alving et al. | 514/8 |
| 4,515,736 | 5/1985 | Deamer | 424/1.1 X |
| 4,598,051 | 7/1986 | Papahadjopoulos et al. | 436/829 X |
| 4,684,625 | 8/1987 | Eppstein et al. | 424/450 X |

Primary Examiner—Richard D. Lovering

[57] ABSTRACT

A composition of liposomes which contain an entrapped pharmaceutical agent and are characterized by: (a) liposome sizes predominantly between about 0.08 and 0.5 microns: (b) at least about 50 mole percent of a membrane-rigidifying component, such as sphingomyelin or neutral phospholipids with predominantly saturated acyl chains: and (c) between about 5–15 mole percent ganglioside $G_{M1}$. The liposomes show a blood/RES tissue distribution ratio, two hours after intravenous administration, which is substantially greater than the sum of the distribution ratios observed with similarly constructed liposome compositions containing the membrane-rigidifying agent alone and gangliosides alone. Also disclosed are methods for enhancing the blood/RES ratio of intravenously administered liposomes, and for assessing the effect of selected liposome components on in vivo uptake of liposomes by cells of the reticuloendothelial system (RES).

5 Claims, 2 Drawing Sheets

LIPOSOMES WITH ENHANCED CIRCULATION TIME

FIELD OF THE INVENTION

The present invention relates to liposome therapeutic compositions, and particularly to liposomal formulations which have enhanced circulation time in the bloodstream, when administered intravenously.

REFERENCES

1. Allen, T. M. (1981) Biochem. Biophys. Acta 640, 385-397.
2. Allen, T. M., and Everest, J. (1983) J. Pharmacol. Exp. Therap. 226, 539-544.
3. Altura, B. M. (1980) Adv. Microcirc. 9, 252-294.
4. Alving, C. R. (1984) Biochem. Soc. Trans. 12, 342-344.
5. Ashwell, G., and Morell, A. G. (1974) Adv. Enzymology 41, 99-128.
6. Czop, J. K. (1978) Proc. Natl. Acad. Sci. USA 75: 3831.
7. Durocher, J. P., et al (1975) Blood 45: 11.
8. Ellens, H., et al. (1981) Biochim. Biophys. Acta 674, 10-18.
9. Gregoriadis, G., and Ryman, B. E. (1972) Eur. J. Biochem. 24, 485-491.
10. Gregoriadis, G., and Neerunjun, D. (1974) Eur. J. Biochem. 47, 179-185.
11. Gregoriadis, G., and Senior, J. (1980) FEBS Lett. 119, 43-46.
12. Greenberg, J. P., et al (1979) Blood 53: 916.
13. Hakomori, S. (1981) Ann. Rev. Biochem. 50, 733-764.
14. Hwang, K. J., et al (1980) Proc. Natl. Acad. Sci. USA 77: 4030.
15. Jonah, M. M., et al. (1975) Biochem. Biophys. Acta 401, 336-348.
16. Juliano, R. L., and Stamp, D. (1975) Biochem. Biophys. Res. Commun. 63, 651-658.
17. Karlsson, K. A. (1982) In: Biological Membranes, vol. 4, D. Chapman (ed.) Academic Press, N.Y., pp. 1-74.
18. Kimelberg, H. K., et al. (1976) Cancer Res. 36, 2949-2957.
19. Lee, K. C., et al, J. Immunology 125: 86 (1980).
20. Lopez-Berestein, G., et al. (1984) Cancer Res. 44, 375-378.
21. Okada, N. (1982) Nature 299: 261.
22. Poznansky, M. J., and Juliano, R. L. (1984) Pharmacol. Rev. 36, 277-336.
23. Richardson, V. J., et al. (1979) Br. J. Cancer 40, 35-43.
24. Saba, T. M. (1970) Arch. Intern. Med. 126, 1031-1052.
25. Schaver, R. (1982) Adv. Carbohydrate Chem. Biochem. 40: 131.
26. Scherphof, T., et al. (1978) Biochim. Biophys. Acta 542, 296-307.
27. Senior, J., and Gregoriadis, G. (1982) FEBS Lett. 145, 109-114.
28. Senior, J., et al. (1985) Biochim. Biophys. Acta 839, 1-8.
29. Szoka, F., Jr., et al (1978) Proc. Natl. Acad. Sci. USA 75: 4194.
30. Szoka, F., Jr., et al (1980) Ann. Rev. Biophys. Bioeng. 9: 467.
31. Woodruff, J. J., et al (1969) J. Exp. Med. 129: 551.

BACKGROUND OF THE INVENTION

Liposome delivery systems have been proposed for a variety of drugs. For use in drug delivery via the bloodstream, liposomes have the potential of providing a controlled "depot" release of a liposome-entrapped drug over an extended time period, and of reducing toxic side effects of the drug, by limiting the concentration of free drug in the bloodstream. Liposome/drug compositions can also increase the convenience of therapy by allowing higher drug dosage and less frequent drug administration. Liposome drug delivery systems are reviewed generally in Poznansky et al.

One limitation of intravenous liposome drug delivery which has been recognized for many years is the rapid uptake of blood-circulating liposomes by the mononuclear phagocytic system (MPS), also referred to as the reticuloendothelial system (RES). This system, which consists of the circulating macrophages and the fixed macrophages of the liver (Kupffer cells), spleen, lungs, and bone marrow, removes foreign particulate matter, including liposomes, from blood circulation with a half life on the order of minutes (Saba). Liposomes, one of the most extensively investigated particulate drug carriers, are removed from circulation primarily by Kupffer cells of the liver and to a lesser extent by other macrophage populations.

A variety of studies on factors which effect liposome uptake by the RES have been reported. Early experiments, using heterogeneous preparations of multilamellar liposomes (MLV) containing phosphatidylcholine (PC) and cholesterol (CH) as their principal lipid constituents, demonstrated that these liposomes are rapidly removed from circulation by uptake into liver and spleen in a biphasic process with an initial rapid uptake followed by a slow phase of uptake (Gregoriadis, 1974; Jonah; Gregoriadis, 1972; Juliano). Half-time for removal of MLV from circulation was on the order of 5-15 min. following intravenous (i.v.) injection. Negatively charged liposomes are removed more rapidly from circulation than neutral or positively charged liposomes. Small unilamellar liposomes (SUV) are cleared with half-lives approximately three- to fourfold slower than MLV (Juliano; Allen, 1983). Uptake of liposomes by liver and spleen occurs at similar rates in several species, including mouse, rat, monkey, and human (Gregoriadis, 1974; Jonah; Kimelberg, 1976; Juliano; Richardson; Lopez-Berestein).

Liposomes which are capable of evading the RES would have two important benefits. One is the increased liposome circulation time in the blood, which would both increase the pharmacokinetic benefits of slow drug release in the bloodstream, and also provide greater opportunity for tissue targeting where the liver, spleen, and lungs are not involved. The second benefit is decreased liposome loading of the RES. In addition to the role of the RES in removing foreign particles, the RES is involved in several other functions, including host defense against pathogenic micro-organisms, parasites, and tumor cells, host responses to endotoxins and hemorragic shock, drug response, and responses to circulating immune complexes (Saba, Altura). It is important, therefore, in liposome administration via the bloodstream, to avoid compromising the RES seriously, by massive short-term or accumulated liposome uptake.

One approach which has been proposed is to increase liposome circulation time by increasing liposome stability in serum. This approach is based on studies by the inventor and others which have shown that factors which decrease leakage of liposome contents in plasma also decrease the rate of uptake of liposomes by the RES (Allen, 1983; Gregoriadis, 1980; Allen, 1981; Senior, 1982). The most important factor contributing to this effect appears to be bilayer rigidity, which renders the liposomes more resistant to the destabilizing effects of serum components, in particular high density lipoproteins (Allen, 1981; Scherphof). Thus, inclusion of cholesterol in the liposomal bilayer can reduce the rate of uptake by the MPS (Gregoriadis, 1980; Hwang; Patel, 1983; Senior, 1985), and solid liposomes such as those composed of distearoylphosphatidylcholine (DSPC) or containing large amounts of sphingomyelin (SM) show decreased rate and extent of uptake into liver (Allen, 1983; Ellens; Senior, 1982; Hwang).

However, this approach appears to have a very limited potential for increasing liposome circulation times in the bloodstream. Studies carried out in support of the present invention, and reported below, indicated that 0.4 micron liposomes containing optimal membrane-rigidifying liposome formulation are predominantly localized in the MPS two hours after intravenous liposome administration. Although longer circulation times are achieved with small unilamellar vesicles or SUVs (having a size range between about 0.03-0.08 microns), SUVs are generally less useful in drug delivery due to their smaller drug-carrying capacity and their tendency to fuse to form large heterogeneous-size liposomes.

Several groups, including the inventor's, have also explored the possibility of increasing liposome circulation times by designing the liposome surface to mimic that of red blood cells. The role of cell surface carbohydrates in cellular recognition phenomena is widely appreciated (Ashwell, Hakomori, Karlsson). The chemistry, metabolism, and biological functions of sialic acid have been reviewed (Schauer). Surface sialic acid, which is carried by gangliosides, and glycoproteins such as glycophorin, plays an important role in the survival of erthrocytes, thrombocytes, and lymphocytes in circulation. Enzymatic removal of sialic acid, which exposes terminal galactose residues, results in rapid removal of erythrocytes from circulation, and uptake into Kupffer cells of the liver (Durocher). Desialylation of thrombocytes (Greenberg) and lymphocytes (Woodruff) also results in their rapid removal by the liver.

Although desialylated erythrocytes will bind to Kupffer cells or peritoneal macrophages in vitro in the absence of serum, serum must be added in order for significant phagocytosis to occur. The nature of the serum components mediating endocytosis is speculative, but immunoglobin and complement (C3b) are thought to be involved. Czop et al. (Czop) have shown that sheep erythrocytes, which are not normally phagocytosed by by human monocytes, will bind C3b and be phagocytosed upon desialylation. Okada et al. (Okada) have demonstrated that sialyglycolipids on liposome membranes restrict activation of the alternative complement pathway and that removal of the terminal sialic acid from the glycolipids abolishes this restricting capacity and results in activation of the alternative complement pathway. Sialic acid, therefore, may be functioning as a non-recognition molecule on cell membranes partly through its ability to prevent binding of C3b, thus preventing phagocytosis via the alternative complement pathway. Other immune factors may also be involved in liposome phagocytosis. Alving has reported that 50% of the test sera from individual humans contain naturally occurring "anti-liposome" antibodies which mediated complement-dependent immune damage to liposomes.

The observations reported above suggest that surface sialic acid, and/or other red-cell surface agents, incorporated into liposomes, for example, in the form of ganglioside or glycophorin, may lead to increased circulation half-lives of liposomes. This approach is described, for example, in U.S. Pat. No. 4,501,728 for "Masking of Liposomes from RES Recognition", although this patent does not disclose whether significant RES masking is actually achieved by coating liposomes with sialic acid.

In fact, experiments conducted in support of the present applications indicate that sialic acid, in the form of gangliosides, has a limited ability to extend circulation half lives in vivo in liposomes which are predominantly composed of conventional liposomes lipids, such as egg phosphatidylcholine (egg PC) or egg PC:cholesterol mixtures. In vivo uptake studies on PC:cholesterol:ganglioside liposomes (0.4 microns) indicate that the injected liposomes are localized predominantly in the MPS two hours post administration.

In summary, several approaches for achieving enhanced lipsome circulation times in the bloodstream have been proposed. Heretofore, however, the approaches have produced quite limited improvements in blood circulation times, particularly in liposomes in the 0.1-0.4 micron size range which are generally most desirable for therapeutic drug compositions.

SUMMARY OF THE INVENTION

It is therefore one general object of the present invention to provide an improved liposome composition which gives significantly improved blood circulation times.

A more specific object of the invention is to provide such a composition in which liposomes are predominantly localized in the bloodstream, rather than in the liver and spleen, several hours after liposome administration.

Yet another object of the invention is to provide such a composition containing liposomes predominantly in the 0.1 to 0.4 micron size range.

Still another object of the invention is to provide an in vitro cell culture method for evaluating lipid compositional factors which are important to liposome uptake by the MPS in vivo.

According to one aspect of the invention, it has been discovered that larger liposomes (0.08-0.4 microns) containing a high molar ratio of particular membrane rigidifying agents and between about 5-15 mole percent of a selected type of ganglioside give a much longer blood circulation time than the sum of the circulation times of liposomes containing each component alone. More precisely, the invention includes a composition of liposomes which contain an entrapped pharmaceutical agent and which are characterized by:

(a) liposome sizes predominantly having a selected size between about 0.08 and 0.5 microns, (b) at least about 50 mole percent of a membrane-rigidifying component including either sphingomyelin (SM) and/or neutral phospholipids with predominantly saturated acyl chains, (c) between 5–15 mole percent monosialylganglioside ($G_M$), and (d) an tissue distribution ratio, as measured by the amount of intravenously administered liposomes in the blood divided by the combined amount of administered liposomes in the liver and spleen, when measure 2 hours after intravenous administration of the composition to a subject, which is substantially greater than the sum of the tissue distribution ratios obtained with similarly constructed liposome compositions containing in one case, at least about 50 mole percent of the membrane rigidifying agent, but not $G_M$, and in another case, between 5-15 mole percent of $G_M$, but not the membrane-rigidifying agent.

In a preferred embodiment of the composition, the liposomes are oligolamellar vesicles sized to a selected size range between about 0.1-0.4 microns, the membrane rigidifying agent includes brain sphingomyelin, at a molar ratio of between about 60-80 mole percent, and the ganglioside is $G_{M1}$. The preferred composition also contains little or no cholesterol.

The liposome composition is used, in a liposome drug treatment, to achieve a significantly extended lifetime of liposomes in the bloodstream.

In another aspect, the invention includes a method of assessing the effect of a selected membrane component on the in vivo uptake of liposomes by the reticuloendothelial system. The method is based on the discovery that cultured macrophages, such as bone marrow macrophages, show a discrimination in liposome uptake which is related to the same liposome composition factors which effect liposome uptake by the MPS in vivo.

These and other objects and features of the invention will become more fully apparent when the following detailed description of the invention is read in conjunction with the accompany figures and examples.

DETAILED DESCRIPTION OF THE INVENTION

The liposome composition of the invention is designed for delivering a drug or other agent, such as nutritional supplements, vitamins, or chelated metal, to a subject via the bloodstream, and for relatively slow uptake of the lipsomes by the MPS, allowing the drug or agent to be released from the liposomes into the bloodstream over an extended period of several hours or more. Alternatively, the composition is designed, by appropriate surface modification of the liposomes, for targeting via the bloodstream to non-MPS target tissues, to allow the drug or agent to concentrate in the immediate region of the target tissue.

Section IA below describes the general method used to evaluate liposome uptake by the MPS in vivo, section IB, the combination of liposome components which have been found, according to one aspect of the invention, to give high blood circulation times for intravenously injected liposomes, and section IC, methods for preparing, sizing, and sterilizing drug-containing liposomes designed for intravenous administration. The utility of the liposome composition, in drug delivery and drug targeting, is discussed in Section II. A novel in vitro system for evaluating liposomal factors which effect liposomal uptake by the MPS in vivo is presented in Example III.

I. PREPARING THE LIPOSOMAL COMPOSITION

A. Measuring liposome uptake by the MPS in vivo

The method used for evaluating liposome circulation time in vivo measures the distribution of intravenously injected liposomes in the bloodstream and the primary organs of the MPS at selected times after injection. In the standardized model which is used, MPS uptake is measured by the ratio of total liposomes in the bloodstream to total liposomes in the liver and spleen, the principal organs of the MPS. In practice, female ICR mice are injected i.v. through the tail vein with a radiolabeled liposome composition, and each time point is determined by measuring total blood and combined liver and spleen radiolabel counts. Total blood counts are calculated by assuming that the total blood volume makes up 7% of the animal's body weight. The experimental methods are detailed in Example 2.

Since the liver and spleen account for nearly 100% of the initial uptake of liposomes by the MPS, the blood/MPS ratio just described provides a good approximation of the extent of uptake from the blood to the MPS in vivo. For example, a ratio of about 1 or greater indicates a predominance of injected liposomes remaining in the bloodstream, and a ratio below about 1, a predominance of liposomes in the MPS. For many of the lipid compositions of interest, blood/MPS ratios were calculated at one-half hour and at two hours, to identify lipid compositions which were effective in both short-term evasion of the MPS, and to evaluate the rate of MPS uptake shortly after injection. For some formulations of interest, blood/MPS ratios during a 24 hour period post injection were also measured, to demonstrate long-term MPS-evasion. As will be seen, only a few prior art formulations gave blood/MPS ratios greater than 1 at one-half hour, and none at two hours. By contrast, the formulations of the invention typically gave blood/MPS ratios of 3–5 after 2 hours and greater than 1 at 24 hours.

It is assumed that the data obtained with the model animal system can be reasonably extrapolated to humans and veterinary animals of interest. This is because, as mentioned above, uptake of liposomes by liver and spleen has been found to occur at similar rates in several mammalian species, including mouse, rat monkey, and human (Gregoriadis, 1974; Jonah; Kimelberg, 1976; Juliano; Richardson; Lopez-Berestein). This result likely reflects the fact that the biochemical factors which appear to be most important in liposome uptake by the RES—including serum lipoproteins, and cell shielding by carbohydrate moieties—are common features of all mammalian species which have been examined.

B. Lipid Components

As indicated above, membrane-rigidifying components, such as SM, cholesterol and saturated lipids, have been proposed heretofore in the context of increased liposome circulation times in the bloodstream. The effects of SM on egg PC liposomes was examined in studies which are reported in part in Examples 3 and 4. With reference to Table 1 in Example 3, it is seen that addition of increasing amounts SM to 0.4 micron oligolamellar vesicles (REVs) increased blood/MPS ratios at two hours progressively from 0.01, in liposomes composed of egg PC alone, to 0.57, in liposomes containing 80 mole percent SM. Brain and egg SM, which are both composed of partially unsaturated hydrocarbon chains, gave higher blood/MPS values than SM with saturated chains, such as stearoyl and palmitoyl chains.

It is known that the polar head groups of SM are able to hydrogen bond with each other and with the head groups of PC, and this feature may be important to the ability of SM to rigidify lipid bilayer structures. If so, the lower blood/MPS ratios seen with highly saturated SMs may be due to the formation of SM domains which are in a non-fluid phase at physiological temperature, and therefore either leakier and/or unable to form polar-region hydrogen bonding Liposomes containing egg PC and increasing mole ratios of distearoylPC (DSPC) also gave increasing blood/MPS values at two hours, but not as high as was seen with brain SM.

Addition of cholesterol (CH) to egg PC liposomes also increased blood/MPS ratios at two hours, but only about one-fifth the increase seen with brain SM, and addition of cholesterol to rigidified liposomes (containing SM and PC) reduced the blood/MPS values observed with SM:PC alone. This result is consistent with the proposed role of membrane rigidity in liposome uptake by the MPS, since cholesterol produces a rigidifying effect on egg PC liposomes, but a fluidizing effect on SM:PC liposomes. It is also noted, from the data in Table 1, that negatively charged phospholipids, such as phosphatidylserine (PS) and phosphatidic acid (PA) substantially negate the increased blood/MPS ratios produced by brain SM.

Several gangliosides, including monosialylganglioside $M_1$ ($G_{M1}$), asialylganglioside, produced by desialylation of $G_{M1}$, disialylganglioside ($G_{D1a}$), and sulfatides were examined for their ability to increase blood/MPS ratios in egg PC and egg PC:cholesterol liposomes (0.4 micron REVs). The studies were designed to determine if one or more gangliosides could increase liposome circulation time significantly, as has been previously proposed, and if so, optimal concentrations of gangliosides, with emphasis on 0.4 micron oligolamellar vesicles. The results, some of which are reported in Examples 4 and 5 below, can be summarized as follows: (1) Addition of $G_{M1}$ to egg PC or egg PC:cholesterol increased blood/MPS ratios after two hours, but to a lesser extent than did SM. (2) Optimal $G_{M1}$ concentration was between about 5–7 mole percent for egg PC:cholesterol liposomes. (3) The enhanced blood/MPS value seen with $G_{M1}$ is substantially abolished by desialylating the liposomes with neuraminidase. (4) Monosialylganglioside gave substantially higher blood/MPS values than did disialylgangliosides and sulfatides.

The ability of $GM_1$ to enhance liposome blood levels was studied during a 24 hour period was also examined. A plot of blood/MPS ratios for PC:CH:$G_{M1}$ liposomes is shown in solid circles in FIG. 1. As seen, the liposomes are largely removed from circulation after 2 hours, and substantially completely removed after 6 hours.

The above data on membrane-rigidifying agents and gangliosides indicate a rather limited ability of these lipid components by themselves to retard liposome uptake by the MPS. The best membrane-rigidifying composition gave blood/RES values of about 0.57, for 0.4 micron oligolamellar vesicles two hours post injection, and the best ganglioside composition, blood/MPS gave values of about 0.3 for the same conditions.

According to an important feature of the invention, it has been discovered that a liposome composition formulated to include (a) at least about 50 mole percent membrane-rigidifying components which is either SM or a saturated neutral phospholipid, and (b) 5–15 mole percent of monosialylganglioside, gives much higher blood/MPS ratios than the sum of the ratios which would be expected from either component alone. That is, the blood/MPS ratio of the combined-component liposomes is substantially higher than that of liposomes containing optimal membrane-rigidifying agents alone plus that achieved with optimal ganglioside components alone.

Several studies on the blood/MPS ratios seen with SM and or DSPC and $G_{M1}$ are reported in Example 4. With particular reference to Table 3 in the example, which shows ratios for 0.4 micron REVs at two hours post injection, it is seen that SM:PC:CH:$G_{M1}$ liposomes give blood/MPS ratios which are over 3 times the sum of the ratios seen with similarly constructed liposomes containing either SM alone and $G_{M1}$ alone. The term "similarly constructed liposomes" is applied herein to denote liposomes which are identical in all respects except for membrane-rigidifying and/or ganglioside components.

Even more dramatic increases in liposome circulation time are observed in liposomes containing SM and $G_{M1}$, in the absence of cholesterol. Here blood/MPS ratios of about 5 times the sum of the ratios seen with similarly constructed liposomes containing either SM alone and $G_{M1}$ alone were observed.

The data in Table 3 also shows the relatively poor increases in blood/MPS ratios which can be achieved with SM in combination in $G_{D1a}$ or sulfatide.

The data in Table 4 of Example 3 show blood/MPS ratios which are observed when DSPC is substituted entirely or in part for SM. The data indicate that DSPC is less effective than brain SM in enhancing liposome circulation time, but that DSPC is also less sensitive to the "inhibitory" effect of cholesterol on blood/MPS values.

The optimal concentration of $G_{M1}$ was determined using the SM:PC, 4:1 formulation which appears to give the highest blood/MPS ratios when combined with $G_{M1}$. The results are plotted in FIG. 2, where blood/MPS ratios determined on the basis of total radioactivity counts (solid circles) and counts corrected for loss of liposomal counts over two hours (open circles) are plotted. The plots show that $G_{M1}$ concentrations between about 7 and 15 mole percent are optimal. Details of the study are provided in Example 5.

Figures 1, 2:
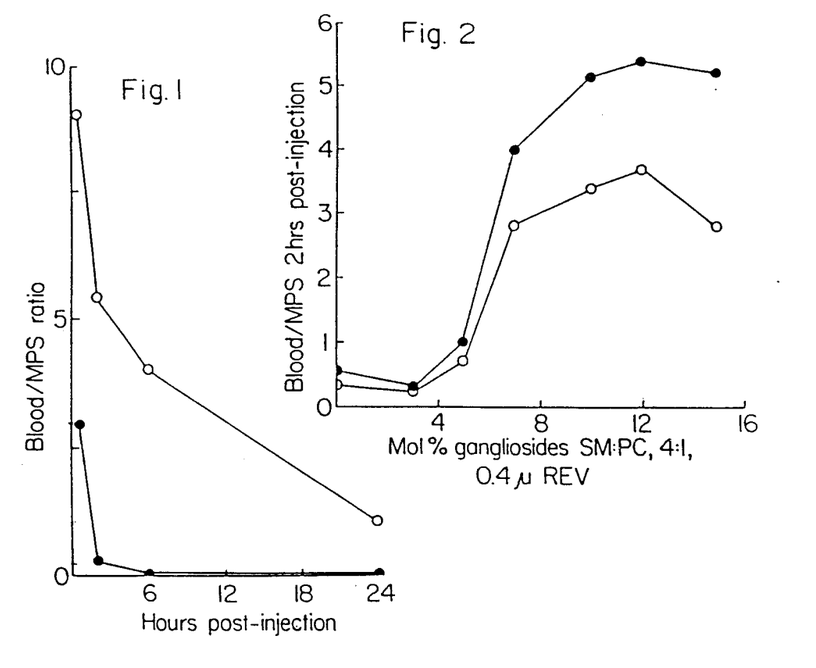
FIG. 1 shows the time course of decrease of blood/MPS ratios in a test subject injected i.v. with (1) liposomes containing ganglioside $G_{M1}$, but not SM (solid circles) and (2) with liposomes containing both $G_{M1}$ and SM (open circles)
FIG. 2 shows the change in blood/MPS two hours post injection, in liposomes containing SM:PC, 4:1, and increasing molar amounts of $G_{M1}$ (solid circles), and the blood/MPS values multiplied by the percent of total liposome-associated radioactivity remaining two hours post-injection (open circles), to correct for loss of liposome radiolabel in two hours.

When an optimal liposome formulation containing SM:PC:$G_{M1}$, 4:1:0.35 is followed 24 hours post injection, the plot shown in open circles in FIG. 1 is obtained. The plot shows high blood/MPS ratios over 6 hours, and a ratio of about 1 even at 24 hours. PC:CH:$G_{M1}$ liposomes are indicated by solid circles in the FIGURE. Thus it can be appreciated that the improved liposome formulation gives unexpectedly high blood/MPS ratios between 2-24 hours post injection.

In addition to the membrane-rigidifying agents and gangliosides required in the liposome composition, the liposomes may be formulated to include other neutral vesicle-forming lipids which do not significantly compromise the MPS-evasion properties of the liposomes. An obvious example is egg PC which is used in the optimal formulation described above. Although cholesterol, or cholesterol derivatives may be used, the data above indicates that the mole ratio of sterols should be kept well below about 30 mole percent and preferably less than 10 mole percent.

The liposomes may also include protective agents such alpha-tocopherol, or other free-radical inhibitors, to minimize oxidative damage to the liposomes and/or entrapped drug carried in the liposomes.

C. Preparing the Liposome Composition

The liposomes may be prepared by a variety of techniques, such as those detailed in Szoka et al, 1980. One preferred method for preparing drug-containing liposomes is the reverse phase evaporation method described by Szoka et al and in U.S. Pat. No. 4,235,871. In this method, a solution of liposome-forming lipids is mixed with a smaller volume of an aqueous medium, and the mixture is dispersed to form a water-in-oil emulsion. The drug or other pharmaceutical agent to be delivered is added either to the lipid solution, in the case of a lipophilic drug, or to the aqueous medium, in the case of a water-soluble drug. Here it is noted that all lipid and aqueous components should preferably be sterile and pyrogen free. After removing the lipid solvent by evaporation, the resulting gel is converted to liposomes, with an encapsulation efficiency, for a water-soluble drug, of up to 50%. The reverse phase evaporation vesicles (REVs) have typical average sizes between about 2-4 microns and are predominantly oligolamellar, that is, contain one or a few lipid bilayer shells. The method is detailed in Example 1A.

The REVs are readily sized, as discussed below, by extrusion to give oligolamellar vesicles having a maximum selected size preferably between about 0.08 to 0.4 microns. Experiments conducted in support of the present invention indicate that sized oligolamellar vesicles of this type show substantially higher blood/MPS ratios than similar sized multilamellar vesicles (MLVs), and that smaller REVs, e.g., 0.1 micron sizes, give higher ratios than larger REVs, e.g., 0.4 microns. Another advantage of REVs is the high ratio of encapsulated drug to lipid which is possible, allowing greater drug doses to be administered in a given lipid dose.

MLVs, where desired, can be formed by simple lipid-film hydration techniques. In this procedure, a mixture of liposome-forming lipids of the type detailed above dissolved in a suitable solvent is evaporated in a vessel to form a thin film, which is then covered by an aqueous medium. The lipid film hydrates to form MLVs, typically with sizes between about 0.1 to 10 microns. These vesicles show relatively poor blood/MPS ratios, compared with similar-composition REVs or SUVs, but do show the same relationships between lipid composition and blood/MPS ratios. That is, MLVs with the specified membrane-rigidifying and ganglioside components give blood/MPS ratios which are substantially higher than the sum of the ratios observed with MLVs containing one but not the other of the two components. Like REVs, MLVs can be extruded to produce a suspension of smaller, relatively homogeneous-size liposomes, in the 0.1-1.0, and preferably 0.1-0.4 micron size range.

According to one important aspect of the invention, the circulation half life of 0.4 micron REVs, having the above SM:PV:$G_{M1}$ (4:1:0.35) composition is substantially the same as that of SUVs having the same composition. This contrasts with the findings from prior art studies on ganglioside-containing liposomes, which show that smaller vessels, especially SUVs, have substantially longer circulation times than larger vesicles. In fact, experiments conducted in support of the present invention indicate that liposomes containing $G_{M1}$ but not SM show a significant size effect, with SUVs being retained in circulation much longer that 0.4 micron REVs. Thus, the lipid composition of the present invention, comprising both $G_{M1}$ and a membrane tightening component such as SM, serves both to enhance blood circulation times severalfold, and allow high circulation times to be achieved in larger vesicles, which are generally preferred for therapeutic injection.

One effective sizing method for REVs and MLVs involves extruding an aqueous suspension of the liposomes through a polycarbonate membrane having a selected uniform pore size, typically 0.1, 0.2, or 0.4 microns (Szoka). The pore size of the membrane corresponds roughly to the largest sizes of liposomes produced by extrusion through that membrane, particularly where the preparation is extruded two or more times through the same membrane. This method of liposome sizing is used in preparing the 0.1 and 0.4 micron REV compositions described in the examples below. As used herein, the expressions "REVs sized to 0.1 micron" and "REVs sized to 0.4 microns" refer to REV liposome compositions which have been sized by extrusion through 0.1 and 0.4 micron pore size polycarbonate membranes, respectively. A more recent method involves extrusion through an asymmetric ceramic filter. The method is detailed in U.S. patent application for Liposome Extrusion Method, Ser. No. 829,710, filed Feb. 13, 1986 and now U.S. Pat. No. 4,737,323.

Alternatively, the REV or MLV preparations can be treated to produce small unilamellar vesicles (SUVs) which are characterized by sizes in the 0.04-0.08 micron range. However, as indicated above, SUVs have a relatively small internal volume, for delivery of water-soluble drugs, and they tend to fuse to form larger heterogeneous size liposomes with heterodisperse drug leakage and MPS uptake characteristics, and are leakier than REVs or MLVs. SUVs can be produced readily by homogenizing or sonicating REVs or MLVs, as described in Example 1C.

After final sizing, the liposomes can be treated, if necessary, to remove free (non-entrapped) drug. Conventional separation techniques, such as centrifugation, diafiltration, and molecular-sieve chromatography are suitable. The composition can be sterilized by filtration through a conventional 0.45 micron depth filter.

II. UTILITY

The significantly increased circulation half life of liposomes constructed as above can be exploited in two general types of therapeutic or diagnostic liposome compositions. The first composition is designed for sustained release of a liposome-associated agent into the bloodstream by circulating liposomes. As seen above, liposomes constructed according to the invention can be maintained predominantly in the bloodstream up to 24 hours, and therefore sustained released of the drug at physiologically effective levels for up to about 1 day or more can be achieved. The second composition is designed for concentrating a liposome-associated drug or radiotracer material or the like via the bloodstream at a targeted non-MPS tissue site, such as a tumor site. The extended lifetime of the liposomes in the bloodstream makes it possible for a significant fraction of the injected liposomes to reach the target site before being removed from the bloodstream by the MPS.

A variety of drugs or other pharmacologically active agents are suitable for delivery by the liposome composition. One general class of drugs include water-soluble, liposome-permeable compounds which are characterized by a tendency to partition preferentially into the aqueous compartments of the liposome suspension, and to equilibrate, over time, between the inner liposomal spaces and outer bulk phase of the suspension. Representative drugs in this class include terbutaline, albuterol, atropine methyl nitrate, cromolyn sodium, propranalol, flunoisolide, ibuprofin, gentamycin, tobermycin, pentamidine, penicillin, theophylline, bleomycin, etoposide, captoprel, n-acetyl cysteine, verapamil, vitamins, and radio-opaque and particle-emitter agents, such as chelated metals. Because of the tendency of these agents to equilibrate with the aqueous composition of the medium, it is preferred to store the liposome composition in lyophilized form, with rehydration shortly before administration. Alternatively, the composition may be prepared in concentrated form, and diluted shortly before administration. The latter approach is detailed in U.S. patent application for "Liposome Concentrate and Method", Ser. No. 860,528, filed May 7, 1986 and now abandoned.

A second general class of drugs are those which are water-soluble, but liposome-impermeable. For the most part, these are peptide or protein molecules, such as peptide hormones, enzymes, enzyme inhibitors, apolipoproteins, and higher molecular weight carbohydrates are characterized by long-term stability of encapsulation. Representative compounds in this class include calcitonin, atriopeptin, $\alpha$-1 antitrypsin (protease inhibitor), interferon, oxytocin, vasopressin, insulin, interleukin-2, superoxide dismutase, tissue plasminogen activator (TPA), plasma factor 8, epidermal growth factor, tumor necrosis factor, lung surfactant protein, interferon, lipocortin, $\alpha$-interferon and erythropoetin.

A third class of drugs are lipophilic molecules which tend to partition into the lipid bilayer phase of the liposomes, and which are therefore associated with the liposomes predominantly in a membrane-entrapped form. The drugs in this class are defined by an oil/water partition coefficient, as measured in a standard oil/water mixture such as octanol/water, of greater than 1 and preferably greater than about 5. Representative drugs include prostaglandins, amphotericin B, progesterone, isosorbide dinitrate, testosterone, nitroglycerin, estradiol, doxorubicin, beclomethasone and esters, vitamin E, cortisone, dexamethasone and esters, and betamethasone valerate.

For sustained drug-release via the bloodstream, the liposome composition is administered intravenously in an amount which provides a suitable drug dosage over the expected delivery time, typically 12–24 hours. The injection may be given as a single bolus or slowly by i.v. drip, to allow gradual dispersal of the liposomes from the site of injection.

Where it is desired to target the liposomes to a selected non-MPS tissue site, the liposomes are preferably designed for surface recognition of target-site molecules. For example, in the case of targeting to a solid tumor, the liposomes may be prepared with surface-bound tumor recognition molecules, such as antibodies directed against tumor-specific antigens. Methods for coupling molecules of this type are well-known to those in the field. These methods generally involve incorporation into the liposomes of lipid components, such as phosphatidylethanolamine, which can be activated for attachment of surface agents, or derivatized lipophilic compounds, such as lipid-derivatized bleomycin.

In one particular liposome composition which is useful for radioimaging of solid tumor regions, the liposomes are prepared with encapsulated radio-opaque or particle-emission metal, typically in a chelated form which substantially prevents permeation through the liposome bilayer, and carrying surface-bound bleomycin molecules, for preferential liposome attachment to tumor sites.

III. ASSESSING LIPID COMPOSITION FACTORS IN VITRO

The invention includes, in another aspect, a rapid in vitro method for assessing the effect of various lipid composition factors on liposome uptake by the MPS in vivo. This method is based on the discovery that that liposome compositions which are most effective in increasing blood/MPS values in vivo are also most effective in reducing uptake of the liposomes by cultured MPS cells in vitro.

In practicing this aspect of the invention, MPS cells, and preferably bone-marrow macrophages, such as murine bone-marrow macrophages, are isolated and cultured according to standard cell-culture methods, such as outlined in Example 7 below. Radiolabeled liposomes having the selected lipid composition to be tested are added to the cells, and the uptake of radioactivity by the cells measured. To date, three important parameters of the system have been examined. These are liposome uptake characteristics by the cultured cells (a) with increasing uptake times, (b) with increasing amounts of liposome added, and (c) as a function of liposome lipid composition.

Figure 3:
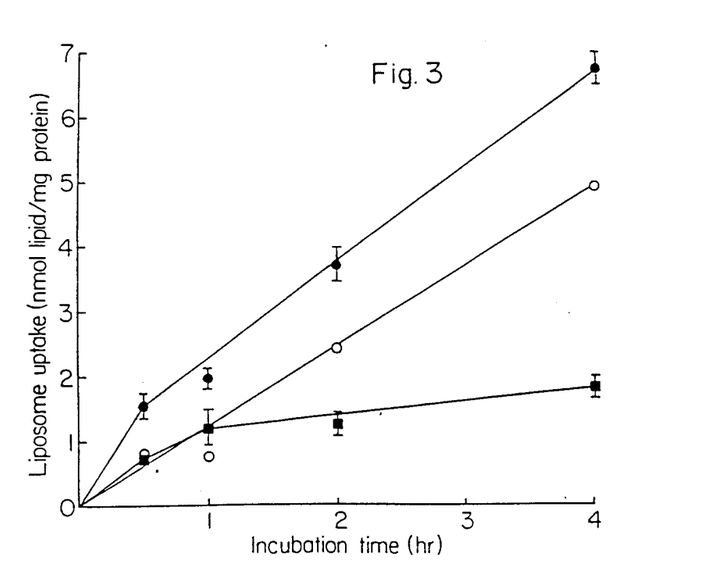
FIG. 3 shows the uptake of PC liposomes by cultured macrophages in vitro, where the solid squares represent non-specific uptake at 4° C., the solid circles, total liposome uptake at 37° C., and the open circles, the difference between total and non-specific uptake; (specific uptake)

FIG. 3 shows the uptake of liposomes by the cells at 37° C. over a 4 hour culture period (solid circles). As seen, the extent of uptake, as measured by nmol of liposome lipid/mg of cell protein, is substantially linear over time. Non-specific uptake by the cells is measured at a cell temperature, preferably about 4° C., where endocytosis does not occur. The solid squares in FIG. 3 shows non-specific uptake. Subtracting the non-specific from the total uptake gives the specific uptake, shown in open circles in the FIGURE.

Figure 4:
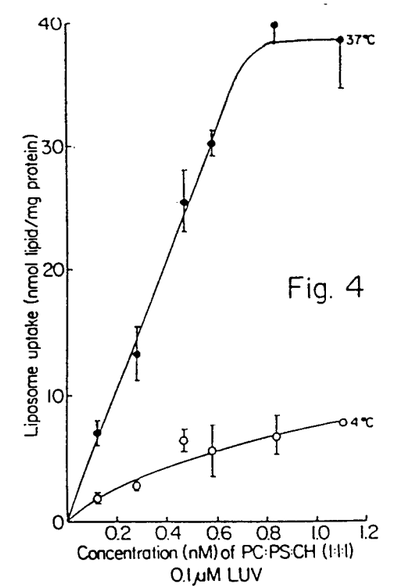
FIG. 4 shows the uptake of liposomes by cultured macrophages in vitro, at increasing concentrations of added liposomes, where the open circles represent non-specific uptake at 4° C., and the the solid circles, total liposome uptake at 37° C.

FIG. 4 shows total (solid circles) and non-specific (open circles) uptake levels with increasing amounts of added liposomes. The system is linearly responsive to increasing liposome concentration, up to a maximum concentration of about 0.8 nmol lipid/mg cell protein. The studies just reported are detailed in Example 7.

The effect of brain SM on the in vitro uptake of egg PC liposomes was examined, in a study reported in Example 8 below. The liposomes tested contained increasing concentrations of SM, from 25 to 75 mole percent. As seen from the data in Table 5 of the example, increasing amounts of SM reduced cell uptake in vitro about 3 fold. The data is consistent with in vivo data presented in Example 3, showing a severalfold increase in blood/MPS ratios in vivo with addition of SM to egg PC liposomes.

Figure 5:
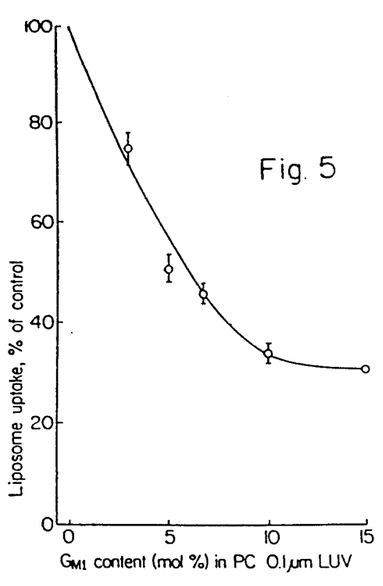
FIG. 5 shows the decline in uptake of PC liposomes, with increasing amounts of $G_{M1}$, by cultured macrophages in culture.

The effect of increasing concentrations of $G_{M1}$ on the in vitro uptake of egg PC liposomes was similarly examined, in the study reported in Example 9 below. The cell uptake data, which are plotted in FIG. 5, show decreasing liposome uptake after 4 hours with increasing amounts of $G_{M1}$, up to a maximum $G_{M1}$ concentration of about 10 mole percent. It will be recalled from above that optimal $G_{M1}$ concentrations in PC:$G_{M1}$ liposomes for in vivo uptake is between about 5–7 mole percent.

Figure 6:
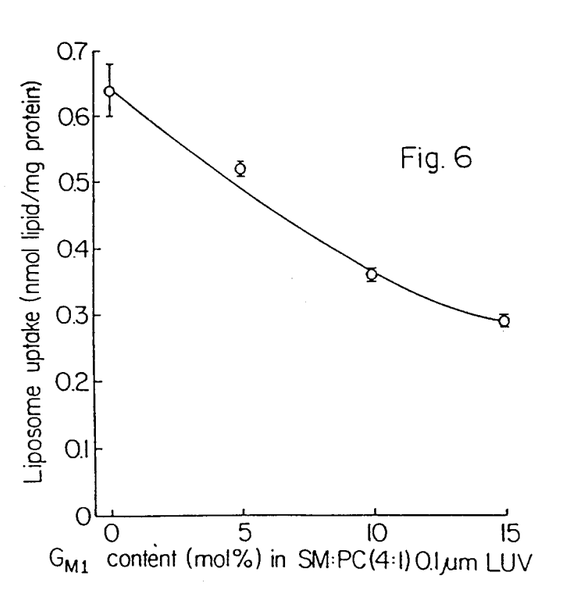
FIG. 6 shows the decline in uptake of SM:PC PC liposomes, with increasing amounts of $G_{M1}$, by cultured macrophages in culture.

A study of the combined effect of SM and $G_{M1}$ on 0.1 oligolamellar PC liposomes is also reported in Example 5. Here increasing amounts of $G_{M1}$ liposomes, up to about 15 mole percent, were added to SM:PC, 4:1 liposomes. The results of the study are shown in FIG. 6. As seen, increasing $G_{M1}$, up to 15 mole percent, decreased in vitro cellular uptake, consistent with the in vivo study reported with respect to FIG. 2.

Studies conducted in support of the present invention also show a rapid increase in cell uptake with increasing PS concentration in PC liposomes, also consistent with the in vivo results presented above.

From the foregoing, it can be appreciated that the in vitro macrophage culture system provides a simple, rapid system for testing lipid composition factors which are important to liposome uptake by the MPS in vivo. It is expected that the system can additionally be used to test the effect of liposome size, lamellar structure, target-related surface components, and drug effects on liposome uptake by the MPS.

The following examples illustrate methods of preparing liposomes with enhanced circulation times, and for accessing circulation times in vivo and in vitro. The examples are intended to illustrate specific liposome compositions and methods of the invention, but are in no way intended to limit the scope thereof.

Materials

Egg phosphatidylcholine (PC), distearoyl PC (DSPC), brain sphingomyelin (SM), phosphatidylserine (PS), and phosphatidic acid (PA) were obtained from Avanti Polar Lipids (Birmingham, AL); and cholesterol and neuraminadase were obtained from Sigma Chemical Co. (St. Louis, MO); [$^{125}$I]-tyraminyl-inulin was made according to published procedures.

EXAMPLE 1

Liposome Preparation

Preparation of REVs, MLVs and SUVs

This example describes the preparation of reverse phase evaporation vesicles (REVs), multilamellar vesicles (MLVs) and small unilamellar vesicles (SUVs) containing egg PC and varying other components including cholesterol, PS, PA, SM, and ganglioside $G_{ML}$ or asialylganglioside.

A. Sized REVs

A total of 50 mg of the selected lipid components, in the mole ratios indicated in the examples below, were dissolved in 5 ml of diethyl ether. An aqueous buffer containing 13 mM phosphate, 140 mM NaCl, pH 7.4 was added to the organic solvent to a final volume of 6.5 ml, and the mixture was emulsified by sonication for 1 minute, maintaining the temperature of the solution at or below room temperature. Where the liposomes were prepared to contain encapsulated [$^{125}$I] tyraminyl-inulin, such was included in the phosphate buffer at a concentration of about 4 $\mu$Ci/ml buffer.

The ether solvent was removed under reduced pressure at room temperature, and the resulting gel was taken up in 1 ml of the above buffer, and shaken vigorously. The resulting REV suspension had particle sizes, as determined by microsopic examination, of between about 0.1 to 20 microns, and was composed predominantly of relatively large (greater than 1 micron) vesicles having one or only a few bilayer lamellae.

The liposomes were extruded twice through a polycarbonate filter (Szoka, 1978), having a selected pore size of 0.8$\mu$, yielding liposomes with maximum pore size of about 0.8$\mu$. To produce REVs with smaller maximum sizes, e.g., 0.4, 0.2, 0.1, and 0.08$\mu$, the liposomes were additionally extruded twice through a polycarbonate membrane having the selected-size pore size. Non-encapsulated [$^{125}$I] tyraminyl-inulin was removed by passing the extruded liposomes through Sephadex G-50 (Pharmacia).

B. MLVs

A total of 50 mg of the selected lipid components were dissolved in 25 ml tertiary butanol. The dissolved lipid was freeze dried, then 50 ml of saline-buffer containing 13 mM phosphate, 140 mM NaCl, 0.02% EDTA, pH 7.4, was added to the lipid film. Radiolabeled tyraminyl inulin was added to the buffer, as above, when liposomes with encapsulated marker were desired. The MLVs formed on gentle shaking for two hours. Non-encapsulated [$^{125}$I] inulin was removed by molecular sieve chromatography as above. Examination of the MLVs showed heterogeneous sizes between about 0.05 to 20 microns, and a predominance of multi-layered structures.

C. SUVs

About 25 ml of the MLV suspension from above was sonicated by ultrasonic irradiation using a ½ inch saphire-bonded probe, with pulse sonication during 15 minute intervals, under optimal output conditions. Sonication was carried out under a stream of nitrogen with the liposome vessel immersed in ice water. The sonicated vesicles were passed through Sephadex G-50 to remove released, free radiolabeled inulin.

EXAMPLE 2

Measuring Blood/MPS Levels

ICR female mice (20 to 25 g) were given intravenous injections of liposome suspensions or saline by injection into the tail vein. The total amount of material injected was about 0.5 mg liposomes and about $10^6$ cpm of $^{125}I$ tyraminyl inulin in a total injection volume of 0.25 ml. At selected time intervals following injection, the animals were sacrificed by cervical dislocation, blood samples were taken from the heart, and the liver and spleen were removed. The liver and spleen were blot dried, weighted and separately counted directly by gamma scintillation counting. A correction faction was applied to account for blood remaining in the liver and spleen. An aliquot of the blood sample was similarly counted by direct gamma counting. Total blood counts were calculated on the basis of a total blood volume of 7% body weight. The blood/MPS ratio was calculated as total blood counts/total counts of the liver and spleen, and was frequently determined for several other tissues.

The blood/MPS ratios measured over time were corrected for loss of liposomal radiolabel by multiplying the measured blood/MPS ratio by the percent of the total counts remaining in vivo at each time point with respect to liposomal counts measured immediately after injection.

EXAMPLE 3

Effect of SM and Cholesterol on Blood/RES

REVs sized to 0.4 microns and having the liposome composition and mole ratios indicated at the left in Table 1 were prepared as in Example 1. The SM used for the reported studies was brain sphingomyelin, whose hydrocarbon-chain moieties include a mixture of partially unsaturated chains. The liposomes were injected intravenously, and the injected animals sacrificed two hours after after injection. The blood/MPS ratios, calculated as above, are shown at the right in the table. The data indicate that:

(1) Cholesterol (33 mole percent) increased the blood/MPS ratio of liposomes, as measured two hours after i.v. injection, a total of from 0.01. to 0.09 over PC liposomes, while SM (80 mole percent) increased the same ratio about 0.56. Substitution of distearoyl SM, dipalmitoyl SM, and egg Sm for brain SM resulted in substantial decreases in blood/MPS ratios, as measured 2 hours after liposome injection (data not shown).

(2) The enhanced circulation-time effect seen with brain SM was progressively decreased by addition of increasing amounts of cholesterol to the SM:PC liposomes.

(3) The enhanced circulation-time effect produced by either Sm and/or cholesterol was completed negated by addition of either PA and PS.

TABLE 1

| Liposome composition (0.4 μLUV) | Blood/MPS (% or injected) 2 hours post-injection |
| --- | --- |
| PC | 0.01 |
| PC:CH, 2:1 | 0.09 |
| SM:PC, 4:1 | 0.57 |
| SM:PC:CH, 2:1:1.5 | 0.16 |
| SM:PC:CH, 4:1:3 | 0.11 |
| SM:PC:CH, 1:1:1 | 0.01 |
| SM:PC:CH, 4:1:3 | 0.11 |
| SM:PC:CH:PS, 4:1:3:1.5 | 0.01 |

TABLE 1-continued

| Liposome composition (0.4 μLUV) | Blood/MPS (% or injected) 2 hours post-injection |
| --- | --- |
| SM:PC:CH:PA, 4:1:3:1.5 | 0.02 |

EXAMPLE 4

Effect of Gangliosides on Blood/MPS

This example examines the effect of gangliosides, and particularly monosialylgangliosides ($G_M$) on blood/MPS ratios in lipids containing various other lipid components, including membrane-rigidifying components, at one-half and 2 hours after i.v. injection.

A. One-half hour post injection

The effect of $G_{M1}$ on blood/MPS in 0.4 micron REVs containing PC, SM and/or cholesterol was investigated as in Example 3. In two cases, ganglioside-containing liposomes were examined, using asialylganglioside ($ASG_{M1}$) obtained from a commercial source. The liposomes can also be desialyated by neuraminadase treatment, according to known methods (Durocher). Liposome administration and determination of blood/MPS ratios one-half hour post injection were as in Example 3. The results are shown in Table 2.

TABLE 2

| Liposome composition (0.4 μLUV) | Blood/MPS ratio ½ hour post-injection |
| --- | --- |
| PC | 0.01 |
| PC:$G_{M1}$ 2:0.14 | 3.3 |
| PC:CH, 2:1 | 0.3 |
| PC:CH:$G_{M1}$, 2:1:0.14 | 2.9 |
| PC:CH:$ASG_{M1}$, 2:1:0.14 | 0.7 |
| SM:PC, 4:1 | 1.6 |
| SM:PC:$G_{M1}$, 4:1:0.35 | 9.1 |
| SM:PC:$ASG_{M1}$, 4:1:0.35 | 1.5 |
| SM:CH, 2:1 | 1.0 |
| SM:CH:$G_{M1}$, 2:1:0.14 | 3.4 |

The following points can be made from the data:

(1) Addition of $G_{M1}$ to PC alone or to PC:cholesterol increased the blood/MPS ratio to about 3.0.

(2) The effect of $G_{M1}$ is largely abolished by desialylation of the liposomes by neuraminidase.

(3) Including SM in liposomes, at a mole ratio of about 80%, increased blood/MPS ratios to about 1.6.

(4) When both brain SM and $G_{M1}$ are added to liposomes, the blood/MPS ratio is increased to about 9.0, about twice the sum of the effect of $G_{M1}$ alone (3.0) and SM alone (1.6).

(6) SM:CH liposomes are intermediate in blood/MPS ratio between PC:CH and SM:PC liposomes.

(7) Cholesterol (about 30 mole percent) substantially reduced the combined effect of SM and $G_{M1}$ on blood/MPS.

B. Two hours post injection

REVs sized to 0.4 microns and having the lipid composition and molar ratios shown at the left in Table 3 below were examined for blood/MPS ratio two hours post injection. The results are shown at the right in the table. The following conclusions can be drawn from the lood/MPS data:

(1) Two hours after i.v. injection, only liposomes containing SM and $G_{M1}$ together gave blood/MPS ratios greater than 1.

(2) The blood/MPS ratios of liposomes containing both SM and $G_{M1}$ were substantially higher (greater than 5) in the absence of cholesterol, and cholesterol mole ratios of about 50 mole percent or greater substantially abolished the increased blood/MPS effect seen with SM and $G_{M1}$.

(3) Neither disialylganglioside ($G_{Dla}$) nor sulfatide ($SO_4^{--}$) was as effective as $G_{M1}$ in enhancing the blood/MPS ratios of SM:PC:CH liposomes.

(4) The effect of $G_{M1}$ at 0.5 hr in PC:$G_{M1}$ liposomes is greatly diminished by two hours (3.3 vs 0.1).

TABLE 3

| Liposome composition (0.4 μLUV) | Blood/MPS ratio 2 hours post-injection |
|---|---|
| PC:CH, 2:1 | 0.09 |
| PC:CH:$G_{M1}$, 2:1:0.14 | 0.3 |
| PC:$G_{M1}$, 5:0.35 | 0.1 |
| SM:PC:CH, 4:1:3 | 0.1 |
| SM:PC:CH:$G_{M1}$, 4:1:3:0.35 | 1.42 |
| SM:PC:CH:$G_{M1}$, 4:1:5:0.35 | 0.16 |
| SM:PC:CH:$G_{M1}$, 2:1:1.5:0.21 | 0.07 |
| SM:PC, 4:1 | 0.57 |
| SM:PC:$G_{M1}$, 4:1:0.35 | 5.4 |
| SM:$G_{M1}$, 5:0.35 | 5.3 |
| SM:PC:CH:$G_{Dla}$, 4:1:3:0.35 | 0.7 |
| SM:PC:CH:$SO_4$, 4:1:3:0.35 | 0.41 |

C. Effect of DSPC on blood/MPS

Several lipid compositions with varying amounts of brain SM and distearoyl PC (DSPC) were examined, as above, for blood/MPS ratios two hours after injection. The liposomes were 0.4 micron REVs, prepared as in Example 1, with the lipid compositions and molar ratios shown at the left in Table 5. The blood/MPS data show that little improvement in circulation time is achieved by substituting DSPC (a saturated PC) for egg PC (a partially unsaturated PC mixture) in liposomes already containing high amounts of SM, but that DSPC can substitute for SM in liposomes to enhance blood/MPS ratios in the presence of $G_{M1}$.

TABLE 4

| Liposome composition (0.4 μLUV) | Blood/MPS ratio 2 hours post-injection |
|---|---|
| DSPC:PC, 4:1 | — |
| DSPC:$G_{M1}$, 5:0.35 | 1.8 |
| SM:DSPC:$G_{M1}$, 4:1:0.35 | 4.9 |
| SM:DSPC:$G_{M1}$, 1:4:0.35 | 3.1 |
| SM:DSPC:CH:$G_{M1}$, 4:1:3:0.35 | 3.7 |
| SM:PC:CH:$GD_{la}$, 4:1:3:0.35 | 0.7 |
| SM:PC:CH:$SO_4$, 4:1:3:0.35 | 0.41 |

EXAMPLE 5

Time Course of Blood/MPS over 24 Hours

Two liposome compositions examined above for blood/MPS ratios at one-half hour and two hours were further studied for changes in blood/MPS ratios for up to 24 hours after i.v. administration. The two compositions are: (1) 0.4 micron REVs containing PC:CH:$G_{M1}$, 2:1:0.14, and (2) SM:PC:$G_{M1}$, 4:1:0.35. The first formulation showed a decline in blood/MPS ratio to a low level (0.3) within two hours, while the second formulation gave to ratio of about 5.3 after two hours. The behavior of the two formulations over a 24 hour period is shown in FIG. 1 for composition 1 (solid circles) and composition 2 (open circles).

As seen, composition 1 was substantially completely removed after 2 hours, whereas composition 2 remained predominantly in the bloodstream, even at 24 hours post injection.

EXAMPLE 6

Effect of Ganglioside Concentration on Blood/MPS

REVs (0.4 microns) containing SM:PC 4:1 and increasing concentrations of $G_{M1}$, up to 15 mole percent, were prepared as above. The compositions were injected i.v. into mice and blood/MPS ratios two hours post injection were determined as above. The data are plotted in FIG. 2, showing actual blood/MPS ratios measured (solid circles) and actual ratios corrected for loss of radiolabeled material by multiplying actual ratios by the percent of injected radioactivity remaining after 2 hours (open circles).

As seen, optimal blood/MPS levels were achieved between about 7–15 mole percent $G_{M1}$.

EXAMPLE 7

Liposome Uptake by Bone Marrow Macrophages

Murine bone marrow macrophages were obtained by published methods (Lee) and suspended in L-cell conditioning medium containing 10% horse serum, to a cell concentration of about 1.5 $10^5$ cells/ml. The cells were maintained at 37° C. under 95% $O_2$, 5% $CO_2$.

Liposome compositions composed of various lipid components to be tested were prepared by as in Example 1, except that $^{14}C$ dipalmitoyl PC (DPPC) (about 0.1 mole percent) was used to radiolabel the liposomes.

The liposome compositions were added to the cells to a final liposome concentration of about 35 nmoles in a total culture volume of 3 mls, i.e., 10 nmoles liposomes per 1.5–2 × $10^6$ cells.

At various time intervals after liposome addition, the culture medium was drawn off and the adhering cultured cells were washed three times with phosphate buffered saline. The cells were loosened from adherence from the culture dish by treatment with 1.0N NaOH, and the cell suspension was counted for radioactivity by conventional $^{14}C$ scintillation counting. Liposome uptake is expressed in terms of nmoles liposome lipid (determined by total DSPC counts per mg macrophage protein.

A control cell culture at 4° C.—a temperature at which macrophages are non-endocytotic—was used to determine levels of non-specific uptake on the various liposome compositions with time. The non-specific uptake radioactivity, also expressed as nmoles liposome lipid/mg macrophage protein, was subtracted from the actual counts measured in the 37° C. culture, to determine actual liposome uptake values.

FIG. 3 shows the liposome uptake of PC:PS:CH, 1:1:2 REVs sizes to 0.1 microns, over a four-hour time period. The three plots represent non-specific uptake by cells cultured at 4° C. (solid squares), total liposome uptake by cells at 37° C. (solid circles), and specific uptake at 37° C. corrected for non-specific uptake (open circles). As seen, corrected specific uptake increases in a substantially linear fashion with time, up to four hours.

FIG. 4 shows plots of non-specific uptake (open circles) and specific uptake (closed circles) measured four hours after liposome addition to the cultured cells, as a function of liposome concentration. Specific liposome uptake increases linearly with increasing amount of liposome, up to about 20 nmole liposomes per mg of cell protein (6 × $10^5$ cells).

EXAMPLE 8

Effect of SM on Liposome Uptake by Macrophages

MLVs composed of PC and SM, at the mole ratios indicated in Table 5 below, were prepared as in Example 1B, and sized to 0.1 micron. The liposomes were added to cultured macrophages, as in Example 7, and the corrected liposome uptake determined for a four hour uptake period. The uptake levels, expressed as nmol lipid/mg cell protein, is shown at the right in the table. As seen, increasing the SM:PC ratio from 1:3 to 3:1 decreased cellular uptake nearly 3 fold.

TABLE 5

| Liposome composition (MLV, 0.1μ) | Liposome uptake |
|---|---|
| SM:PC, 1:3 | 1.74 |
| SM:PC, 1:2 | 1.78 |
| SM:PC, 1:1 | 1.46 |
| SM:PC, 2:1 | 0.90 |
| SM:PC, 3:1 | 0.59 |

EXAMPLE 9

Effect of $G_{M1}$ on Liposome Uptake by Macrophages

A. PC liposomes

REVs sized to 0.1 micron and containing PC and increasing concentrations of $G_{M1}$ were prepared as in Example 1A. Uptake of the REVs by macrophages was measured 4 hours after liposome addition to macrophage culture. FIG. 5 shows the uptake, expressed as a percentage of control (PC alone) REVs. Control values averaged 3.5 nmoles/mg protein. As seen, increasing amounts of $G_{M1}$, up to about 10 mole percent, progressively decreased liposome uptake by the cells, to about 30% of control levels.

B. SM:PC liposomes

REVs sized to 0.1 micron and containing SM:PC, 4:1, and increasing concentrations of $G_{M1}$ were prepared as in Example 1A. Uptake of the REVs by macrophages was measured 4 hours after liposome addition to macrophage culture. FIG. 6 shows the uptake, expressed as nmol lipid uptake/mg cell protein. As seen, increasing amounts of $G_{M1}$, up to about 15 mole percent, progressively decreased liposome uptake by the cells.

While the invention has been described and illustrated with respect to preferred methods and applications, it will be appreciated that various and modifications can be made without departing from the invention.

It is claimed:

1. A liposome composition having an enhanced blood circulation time when administered intravenously, comprising liposomes which contain an entrapped pharmaceutical agent and are characterized by:
   (a) liposome sizes predominantly between about 0.08 and 0.5 microns,
   (b) at least about 50 mole percent of a membrane-rigidifying lipid component selected from the group consisting of sphingomyelin and neutral phospholipids with predominantly saturated acyl chains, and
   (c) between about 5-15 mole precent ganglioside $G_{M1}$.

2. The composition of claim 1, wherein the liposomes have a size distribution produced by liposome extrusion through a 0.4 micron polycarbonate filter.

3. The composition of claim 1, wherein the membrane-rigidifying agent is predominantly PC with saturated acyl chains.

4. In a therapeutic drug treatment in which a drug is administered intravenously in a suspension of liposomes whose sizes are predominantly between about 0.08-0.5 microns, a method of extending the lifetime of liposomes in the bloodstream which comprises preparing the liposomes to contain:
   (a) at least about 50 mole percent of a membrane-rigidifying component selected from the group consisting of sphingomyelin and neutral phospholipids with predominantly saturated acyl chains, and
   (b) between about 5-15 mole percent ganglioside $G_{M1}$.

5. The method of claim 4, wherein the liposomes are predominantly oligolamellar and have a size distribution produced by liposome extrusion through a 0.4 micron polycarbonate filter.

* * * * *